(12) United States Patent
Knight et al.

(10) Patent No.: US 12,075,754 B2
(45) Date of Patent: Sep. 3, 2024

(54) RFID TAG INSERTION CARTRIDGE

(71) Applicant: Somark Group Pty Ltd, Sydney (AU)

(72) Inventors: Adrian Knight, Sydney (AU); Paul Donohoe, Warlingham (GB); Joe Nebolon, San Diego, CA (US); Steve Elliott, Encinitas, CA (US); Alexander Bates, Christies Beach (AU)

(73) Assignee: Somark Group Pty Ltd (AU)

( * ) Notice: Subject to any disclaimer, the term of this patent is extended or adjusted under 35 U.S.C. 154(b) by 284 days.

(21) Appl. No.: 17/634,948

(22) PCT Filed: Aug. 17, 2020

(86) PCT No.: PCT/US2020/046708
§ 371 (c)(1),
(2) Date: Feb. 11, 2022

(87) PCT Pub. No.: WO2021/030807
PCT Pub. Date: Feb. 18, 2021

(65) Prior Publication Data
US 2022/0287270 A1    Sep. 15, 2022

Related U.S. Application Data

(60) Provisional application No. 62/887,415, filed on Aug. 15, 2019.

(51) Int. Cl.
*A01K 11/00* (2006.01)
*A01K 29/00* (2006.01)
*G06K 19/077* (2006.01)

(52) U.S. Cl.
CPC .......... *A01K 11/006* (2013.01); *A01K 29/005* (2013.01); *G06K 19/07758* (2013.01)

(58) Field of Classification Search
None
See application file for complete search history.

(56) References Cited

U.S. PATENT DOCUMENTS 3,658,061 A * 4/1972 Hall .................... A61M 5/3216
                                                           604/263
4,262,632 A    4/1981 Hanton et al.
(Continued)

FOREIGN PATENT DOCUMENTS

CN    105473174 B  * 10/2019  .......... A61M 5/3221
CN    110325231 B  * 10/2020  .......... A61M 11/007
(Continued)

OTHER PUBLICATIONS

PCT International Search Report for PCT/US2020/46708, mailed Nov. 23, 2020, 3 pages.
(Continued)

*Primary Examiner* — Fekadeselassie Girma
(74) *Attorney, Agent, or Firm* — BARNES & THORNBURG LLP; Scott D. Rothenberger

(57) ABSTRACT

A radio frequency identification (RFID) tag insertion cartridge configured for use in implanting a flexible RFID tag into a small animal using a needle-retraction implant tool. In embodiments, the cartridge includes a cartridge housing and a bevel cap. In embodiments, the cartridge housing is configured to receive a carriage portion inserted into a first end of the cartridge housing with a retractable needle extended out of a second end of the carriage portion to present the retractable needle in an extended position with the RFID tag carried within the retractable needle. In embodiments, the bevel cap has a proximal portion with a mating feature configured to mate with the cartridge housing and one or more needle capture elements configured to selectively couple to the needle in the extended position in
(Continued)

a side-mountable manner without a direct axial force being exerted on the needle.

11 Claims, 9 Drawing Sheets

(56) References Cited

U.S. PATENT DOCUMENTS

| | | | | |
|---|---|---|---|---|
| 5,211,129 A | * | 5/1993 | Taylor | G06K 19/0723 600/432 |
| 5,288,291 A | * | 2/1994 | Teoh | A61M 5/178 604/218 |
| 5,632,732 A | * | 5/1997 | Szabo | A61M 5/3216 604/263 |
| 5,772,671 A | * | 6/1998 | Harmon | A61M 37/0069 604/60 |
| 6,974,004 B2 | | 12/2005 | Feist et al. | |
| 8,353,917 B2 | | 1/2013 | Mandecki | |
| 10,010,677 B2 | * | 7/2018 | Shluzas | A61M 5/31515 |
| 10,173,010 B2 | * | 1/2019 | Shluzas | A61J 1/2096 |
| 10,926,036 B2 | * | 2/2021 | Shluzas | A61M 5/3148 |
| 2008/0042849 A1 | * | 2/2008 | Saito | G06K 19/07749 604/272 |
| 2008/0106419 A1 | * | 5/2008 | Sakama | G06K 19/07749 340/572.7 |
| 2016/0037749 A1 | * | 2/2016 | Gandola | A01K 11/005 600/509 |
| 2016/0184725 A1 | * | 6/2016 | Wong | A63H 30/04 446/268 |
| 2016/0206834 A1 | * | 7/2016 | Shluzas | A61M 5/508 |
| 2016/0279333 A1 | * | 9/2016 | Shluzas | A61M 5/31515 |
| 2016/0338798 A1 | * | 11/2016 | Vora | A61B 5/0006 |
| 2019/0125975 A1 | * | 5/2019 | Shluzas | A61M 5/3232 |
| 2021/0244890 A1 | * | 8/2021 | Shluzas | A61M 5/3234 |

FOREIGN PATENT DOCUMENTS

| | | | | |
|---|---|---|---|---|
| JP | | 6811747 B2 * | 1/2021 | A61M 5/001 |
| KR | 10 2009 0058746 | | 6/2009 | |
| KR | 10-1940275 B1 | | 1/2019 | |
| WO | WO 2017/136898 A1 | | 8/2017 | |
| WO | WO-2018085451 A1 * | | 5/2018 | A61M 5/178 |
| WO | WO 2019/071320 A1 | | 4/2019 | |

OTHER PUBLICATIONS

PCT Written Opinion of the ISA for PCT/US2020/46708, mailed Nov. 23, 2020, 9 pages.

* cited by examiner

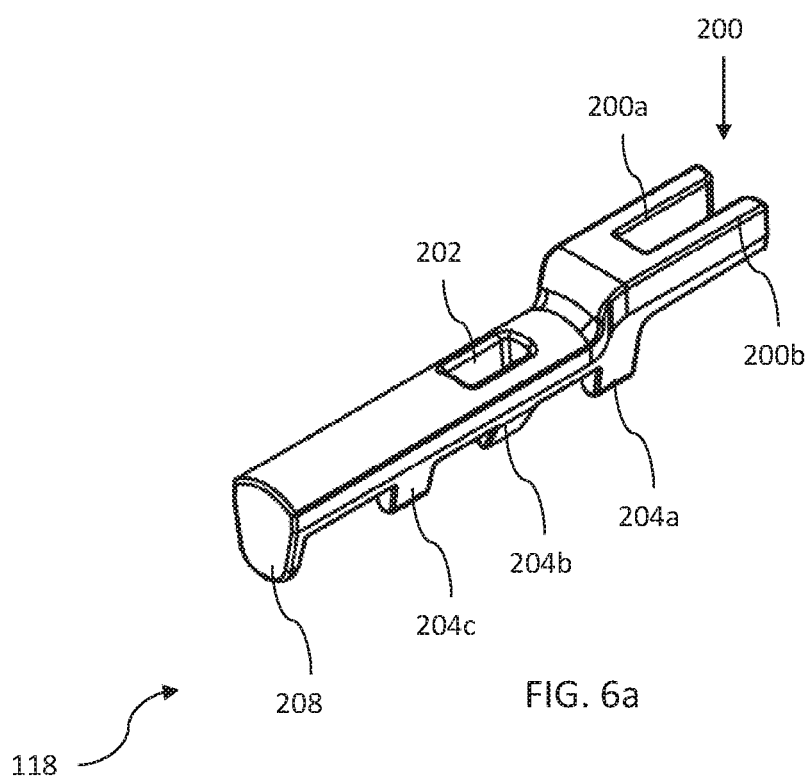

RFID TAG INSERTION CARTRIDGE

RELATED APPLICATIONS

The present application is a National Phase entry of PCT Application No PCT/US2020/045708, filed Aug. 17, 2020, which claims priority from U.S. application Ser. No. 62/887,415, filed Aug. 15, 2019, each of which is hereby fully incorporated herein by reference.

TECHNICAL FIELD

The present disclosure relates generally to implanting radio frequency identification (RFID) animal marking/tracking implants. More particularly, the present disclosure relates to an insertion cartridge configured for introducing an RFID tag into a tail of a rodent.

BACKGROUND

The field of animal research and experimentation benefits from accurate identification and monitoring of each of a plurality of animals. Animal research involving rodents, such as mice or rats, has increased with the advent of genetically engineered strains of these test animals.

A radio-frequency identification (RFID) tag may be used to mark/identify an animal. RFID tags are designed to be small to reduce discomfort to the animal. RFID tags have a radio receiver for receiving the interrogation radio wave and a radio transmitter for transmitting a radio wave comprising identification information in response to the received interrogation radio wave.

Implantable animal tracking RFID tags are conventionally inserted into the animal in a subdermal location. Most implantable RFID tags for animals are in the form of a rigid capsule of a non-conductive material like glass. Examples of these kinds of animal implantable passive RFID tags are shown in U.S. Pat. Nos. 4,262,632, 5,211,129 and 6,974,004, and U.S. Publ. No. US2008/0042849 A1.

With respect to rodents, a subdermal insertion of the RFID tag in the base of the tail is one viable implant location. The insertion procedure conventionally involves an operator using an insertion device to insert a cannulated needle into a restrained animal to implant an RFID tag in a subdermal location in the animal. Unfortunately, both the size and rigid nature of these kinds of RFID tags in a capsule make such needle-based implantation difficult, painful, and ineffective.

A solution to these problems for needle-based implantation of RFID tags is provided by the small, elongated and relatively flexible microelectronic animal identification tags developed by the assignee of the present disclosure that are marketed as the RFAi.D™ tag (www.mysensalab.com/products/rfaid-tag/), various aspects of which are described in U.S. Publ. No. US2016/0037749 A1 and PCT Publ. No. WO2017/136898 A1.

One of the challenges with needle-based implantation of RFID tags is that during transportation and handling the RFID tag must be secured within the cannula of the needle without falling out or being damaged. Various solution to this challenge in terms of plugs, adhesives or retention features internal to the needle for holding the implant in place are described in U.S Pat. Nos. 5,772,671 and 8,353,917. Korean Patent Application No. KR 20090058746 A describes a protective cap placed over the distal tip of the needle with a plug portion securing the RFID tag device within the cannula of the needle.

Some RFID tag insertion tools use a retraction technique for implantation that withdraws the needle to leave the RFID tag in place as opposed to injecting or ejecting the RFID tag from the needle. Such a retraction technique is described in International Patent Application No. WO 2019/071320 A1, including embodiments which describe a retractable needle.

Unfortunately, the prior art solutions for retaining the RFID tag within such a retractable needle are not optimal due to the potential for damage to the needle, the RFID tag, or both. There remains a need for alternative mechanisms to retain an RFID tag device within a needle configured for use with a retraction technique for implanting the RFID tag without damaging the RFID tag or the needle during transport or implantation.

SUMMARY

An improved RFID tag insertion cartridge is disclosed for use in implanting an RFID tag device into a rodent or other animal using a retraction technique. In embodiments, the improved RFID tag insertion cartridge is configured for use with an RFID tag insertion tool having a retractable needle. The improved RFID tag insertion cartridge includes a bevel cap configured to be coupled to a retractable needle of the RFID tag insertion cartridge such that little or no axial force is exerted on the needle during coupling or decoupling of the bevel cap. In this way, the bevel cap is configured for retain and protect the RFID tag device and the needle.

In various embodiments, the bevel cap can be reliably coupled to a retractable needle without risking damage to the needle bevel or compression damage to the RFID tag device. Existing caps that are affixed to a stationary needle by translation of the cap along the axis of the needle may cause a retractable needle to move resulting in damage to the needle bevel and/or the RFID tag device, either of which could be compressed by the cap.

In various embodiments, one or more mechanical features of the bevel cap interact with the needle and insertion cartridge to protect both the needle and the RFID tag device. In some embodiments, the bevel cap includes a plurality of needle capture elements that provide a snap fit engagement with the needle. In some embodiments, a distal portion of the bevel cap is configured to mate with a feature on the cartridge to provide an effective pivot point for rotating a proximal portion of the bevel cap onto the needle. In some embodiments, a shoulder portion of the bevel cap interfaces with a distal end of the housing to position the bevel cap axially relative to the housing and the needle.

The above summary is not intended to describe each illustrated embodiment or every implementation of the subject matter hereof. The figures and the detailed description that follow more particularly exemplify various embodiments.

BRIEF DESCRIPTION OF THE DRAWINGS

Subject matter hereof may be more completely understood in consideration of the following detailed description of various embodiments in connection with the accompanying figures, in which:

FIG. 6a is an isometric view of a bevel cap for use with an RFID tag insertion cartridge, according to embodiments described herein.

Figure 1:
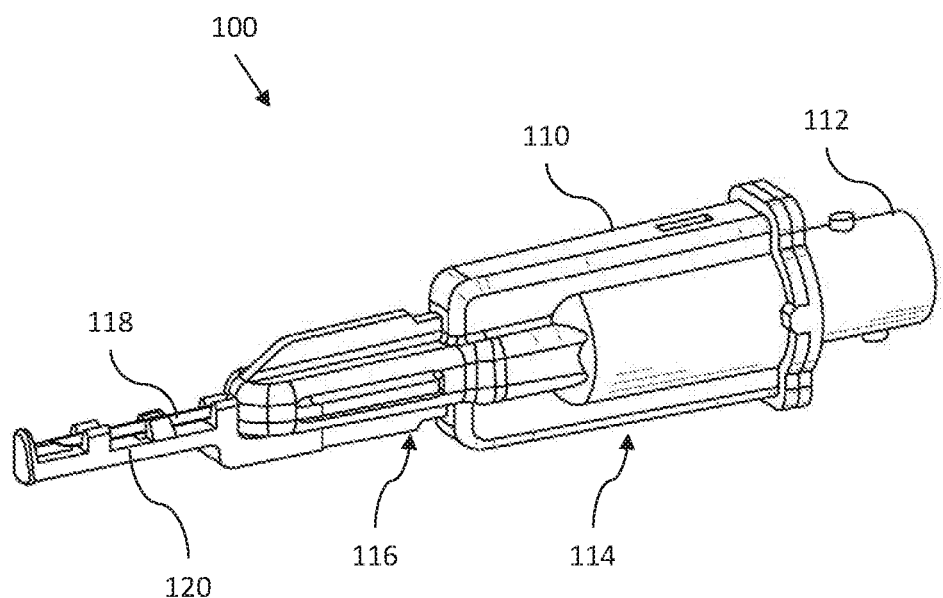
FIG. 1 is an isometric view of an RFID tag insertion cartridge with a bevel cap, according to embodiments described herein.

While various embodiments are amenable to various modifications and alternative forms, specifics thereof have been shown by way of example in the drawings and will be described in detail. It should be understood, however, that the intention is not to limit the claimed inventions to the particular embodiments described. On the contrary, the intention is to cover all modifications, equivalents, and alternatives falling within the spirit and scope of the subject matter as defined by the claims.

DETAILED DESCRIPTION OF THE DRAWINGS

Disclosed herein is an improved RFID tag insertion cartridge for use in implanting an RFID tag device into the base of the tail of a rodent or other animal. The improved RFID tag insertion cartridge also includes a bevel cap configured to be coupled to a needle of the RFID tag insertion cartridge from an angle orthogonal to the cylindrical axis of the needle. The bevel cap is therefore configured to exert little to no axial force on the needle during coupling or decoupling. An example of an insertion tool is shown in International Patent Application No. WO 2019/071320 A1, which is incorporated by reference herein. Embodiments of the improved RFID tag insertion cartridge are configured for use with any passive RFID tags being of appropriate size and operability. For example, the improved RFID tag insertion cartridge can be used with RFID tags as they are described in U.S. Publ. No. US2016/0037749 A1 and PCT Publ. No. WO2017/136898 A1.

While embodiments disclosed herein are described as "RFID insertion" devices (e.g., "insertion cartridge", "insertion tool", etc.), the RFID insertion cartridge and RFID insertion tool are named as such because they aid in implanting an RFID tag within a tail of a rodent. The RFID insertion cartridge and RFID insertion tool do not, however, insert an RFID tag under the skin of rodents, they leave the RFID tag under the skin of the rodent. The actions that the RFID insertion cartridge and RFID insertion tool perform are an injection of an RFID-tag-carrying needle, then a retraction of that needle while holding the RFID tag in place such that the RFID tag is left under the skin of the rodent.

Figure 4:
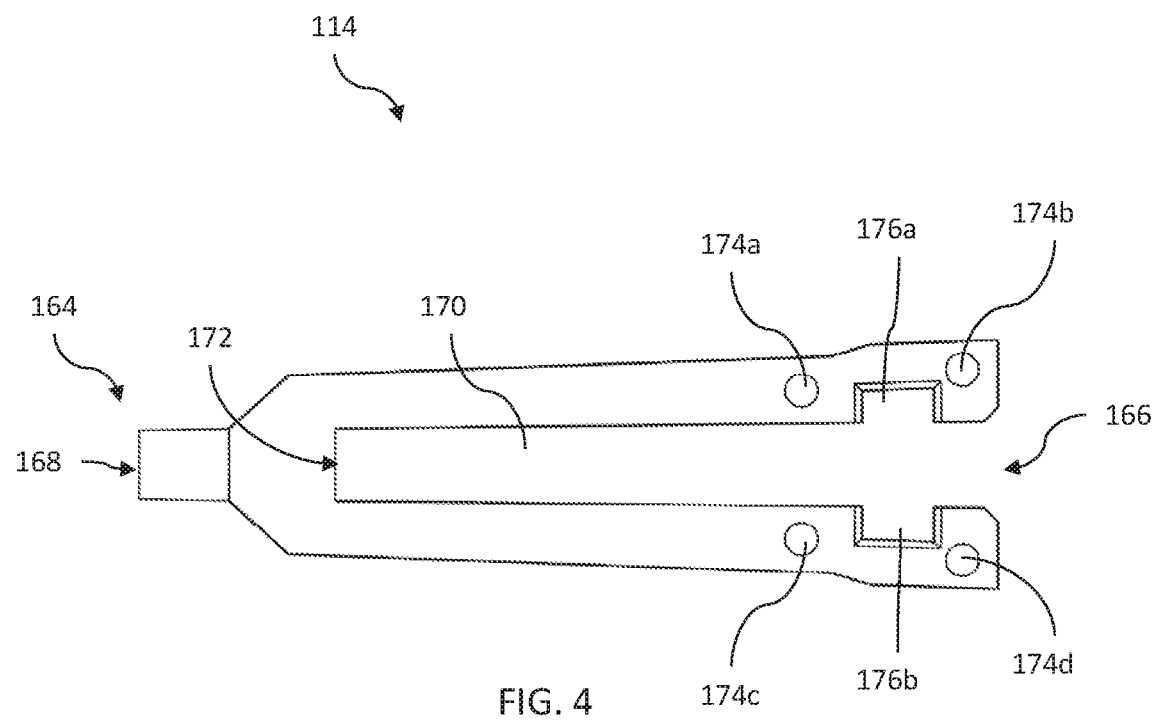
FIG. 4 is an isometric view of a carriage of an RFID tag insertion cartridge, according to embodiments described herein.
Figure 5:
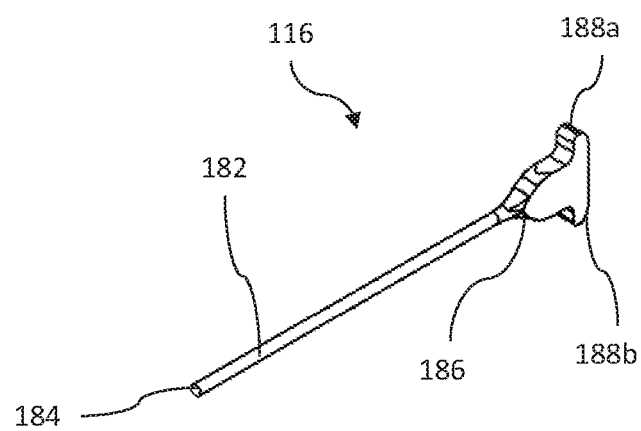
FIG. 5 is an isometric view of a stop pin of an RFID tag insertion cartridge, according to embodiments described herein.

FIG. 1 depicts an improved RFID insertion cartridge 100. Cartridge 100 includes a cartridge housing 110 coupled to a cartridge coupling 112. In embodiments, housing 110 further includes a carriage 114, as depicted in FIGS. 4 and 7, and a stop pin 116, as depicted in FIGS. 5 and 7, contained within housing 110. Cartridge 100 also includes a needle 118 and a bevel cap 120.

Needle 118 can be sized between 19 and 23 American wire gauge in diameter and made of medical grade stainless steel or other suitable materials. In embodiments, needle 118 can include an incision depth mark to aid a user in judging depth of incision. Further, the distal tip of needle 118 includes a sharp edge created via bevel-cut opening.

Figure 2:
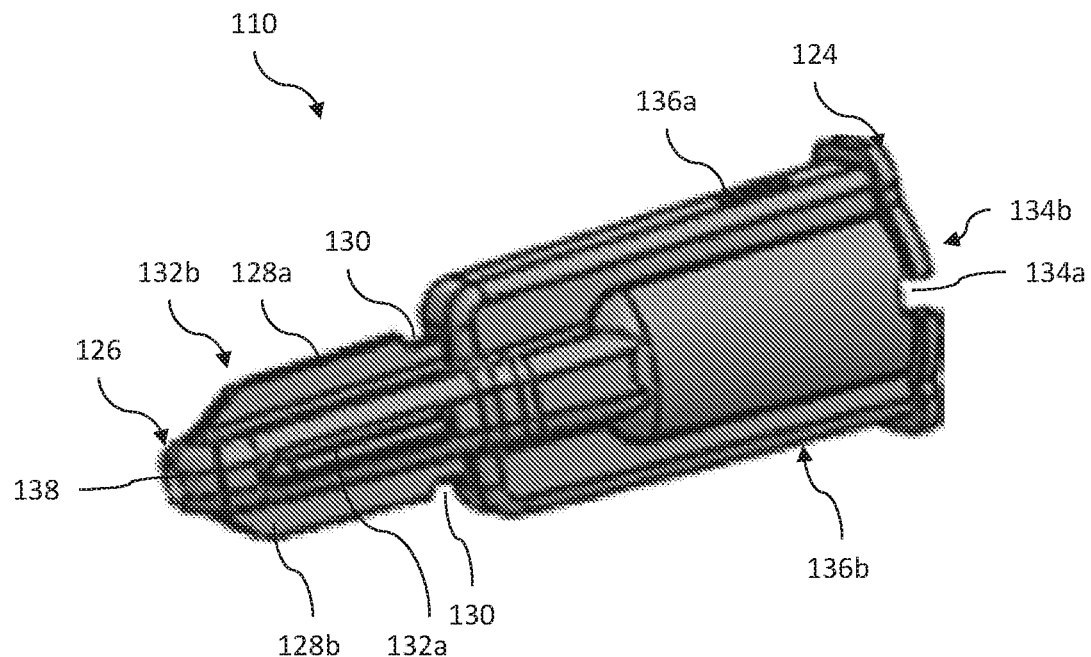
FIG. 2 is an isometric view of a housing of an RFID tag insertion cartridge, according to embodiments described herein.

As depicted in FIG. 2, housing 110 includes a first end 124 and a second end 126. Housing 110 also includes primary alignment flanges 128a and 128b arranged proximal to second end 126. Primary alignment flanges 128a and 128b further include a safety cap notch 130 configured for providing a coupling structure for various safety caps. Housing 110 also includes secondary alignment flanges 132a and 132b arranged proximal to second end 126. Secondary alignment flanges 128a and 128b further can also include various features for providing coupling and support structure for various safety caps. In one embodiment, primary alignment flanges 128a and 128b are arranged opposite each other and perpendicular to secondary alignment flanges 132a and 132b. In other embodiments, more or less than 4 alignment flanges can be included proximal second end 126.

Housing 110 also includes coupling alignment notches 134a and 134b, and coupling wedge apertures 136a and 136b. Coupling alignment notches 134a and 134b can be arranged at the first end 124. Coupling alignment notches 134a and 134b are configured for engaging and aligning with cartridge coupling 112. Coupling wedge apertures 136a and 136b can be arranged proximal the first end 124. Coupling wedge apertures 136a and 136b are configured for coupling with cartridge coupling 112. Housing 110 also includes a needle aperture 138 at a second end 126 of housing 110. Needle aperture 138 is sized and shaped to guide and support needle 118. Needle aperture 138 can also be sized and shaped to allow axial movement of needle 118 to permit retraction of needle 118 during the implantation procedure.

Figure 3:
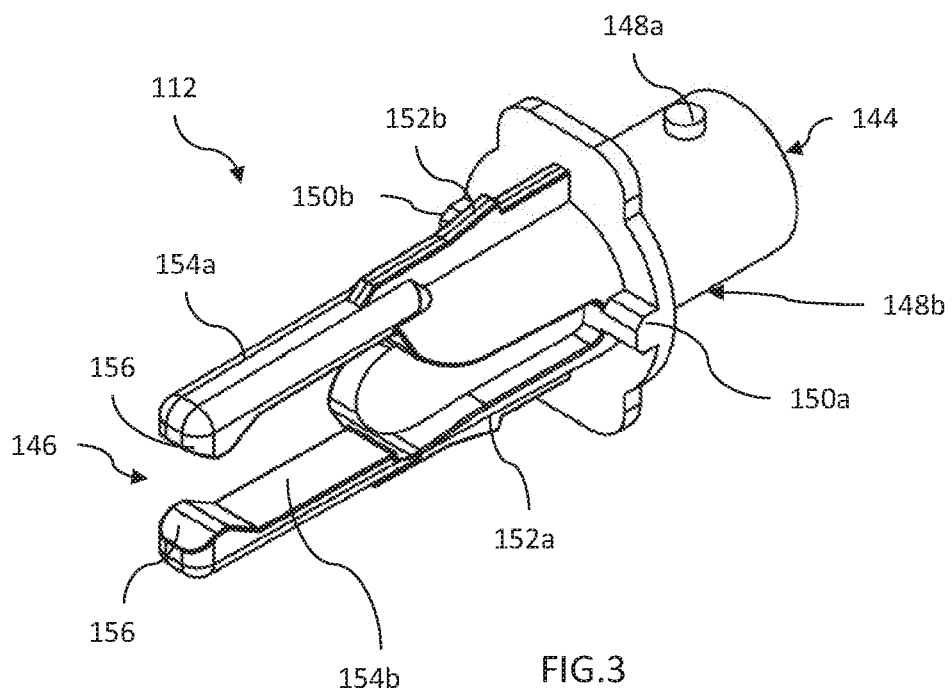
FIG. 3 is an isometric view of a coupling of an RFID tag insertion cartridge, according to embodiments described herein.

As depicted in FIG. 3, coupling 112 includes a first end 144 and a second end 146. Coupling 112 further includes tool coupling bosses 148a and 148b arranged proximal first end 144. As depicted in FIG. 1, coupling bosses 148a and 148b are asymmetrically arranged on coupling 112. In embodiments, the asymmetrical arrangement of coupling bosses 148a and 148b ensures proper orientation of cartridge 100 to an RFID insertion tool as is depicted in WO 2019/071320 A1.

Coupling 112 also includes coupling alignment tabs 150a and 150b and coupling wedges 152a and 152b. In embodiments, coupling alignment tabs 150a and 150b are sized and shaped to engage with the corresponding coupling alignment notches 134a and 134b of housing 110. Further, coupling wedges 152a and 152b are configured to be received within the corresponding coupling wedge apertures 136a and 136b of housing 110 to form a snap fit coupling. Coupling wedges 152a and 152b are sized and shaped such that coupling 112 can be press fit into housing 110 during assembly but cannot be easily disassembled thereafter. During assembly, coupling alignment tabs 150a and 150b are received within coupling alignment notches 134a and 134b of housing 110 to aid in proper alignment during assembly of coupling 112 to housing 110.

At second end 146, coupling 112 include stop pin tabs 154a and 154b projecting from first end 144 to second end 146. Stop pin tabs 154a and 154b comprise cantilevered columns projecting from first end 144 such that stop pin tabs 154a and 154b can be elastically deformed at the distal tips. Each stop pin tab 154a and 154b further includes a tab projection 156. Tab projection 165 of stop pin tabs 154a and 154b are configured to elastically engage with stop pin 116. Tab projections 165 and stop pin tabs 154a and 154b are shaped to allow stop pin 116 to move axially only when stop pin 116 is forced into motion by carriage 114.

As depicted in FIG. 4, carriage 114 includes a first end 164 and a second end 166. At second end 166, carriage 114 includes a needle mount aperture 168. Needle mount aperture 168 is configured to receive needle 118 such that needle 118 is fixed to carriage 114 at needle mount aperture 168. Carriage 114 also includes a stop pin channel 170 and a stop pin engaging surface 172. In embodiments, stop pin channel 170 is configured to guide axial movement of stop pin 116. Stop pin engaging surface 172 is arranged near second end 166 and is configured to serve as a mechanical stop for stop pin 116.

At first end 164, carriage 114 further includes protrusions 174a-174d. Protrusions 174a-174d are configured to slidably engage with interior surfaces of housing 110. Thus, protrusions 174a-174d serve to guide axial movement of carriage 114 within housing 110. Carriage 110 also includes tool coupler notches 176a and 176b arranged at first end 164. Tool coupler notches 176a and 176b are configured to be engaged with an RFID insertion tool such as is depicted in WO 2019/071320 A1.

As depicted in FIG. 5, stop pin 116 includes a shaft 182 and a tag stop surface 184 arranged at the distal tip of shaft 182. Shaft 182 is sized and shaped to be slidably received within needle 118. Tag stop surface 184 is configured to provide a mechanical stop for the RFID tag when the RFID tag is loaded into needle 118. Stop pin 116 also includes a carriage engaging surface 186 and coupling engaging tabs 188a and 188b. Carriage engaging surface 186 is configured to engage with stop pin engaging surface 172 of carriage 114. During axial motion of carriage 114 towards first end 124 of housing 110, carriage 114 reaches a point of travel where stop pin engaging surface 172 of carriage 114 engages with carriage engaging surface 186 of stop pin 116 and both carriage 114 and stop pin 116 continue axial motion towards first end 124 of housing 110. Coupling engaging tabs 188a and 188b are configured to engage with tab projections 156 of stop pin tabs 154a and 154b of coupling 112. Prior to axial motion of stop pin 116 and carriage 114 towards first end 124 of housing 110, stop pin tabs 154a and 154b of coupling 112 hold stop pin 116 in a distal position.

Figure 6B:
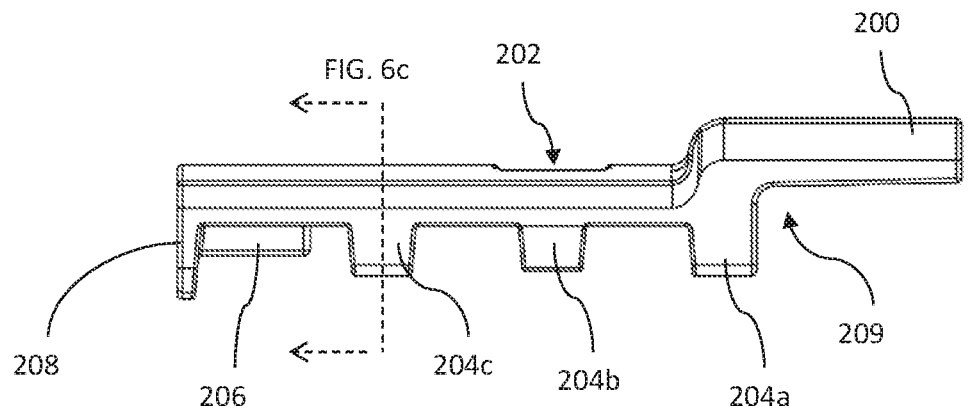
FIG. 6b is a side view of a bevel cap for use with an RFID tag insertion cartridge, according to embodiments described herein.
Figure 6C:
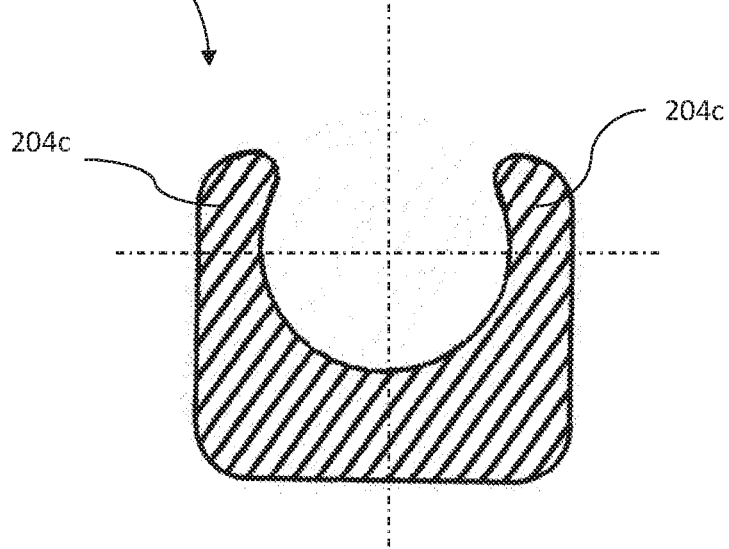
FIG. 6c is a cross-sectional end view of the bevel cap of FIG. 6b.

As depicted in FIG. 6a-6c, bevel cap 120 includes a housing mating feature 200 as a proximal portion. In embodiments, housing mating feature 200 is configured as a pair of fork elements 200a and 200b configured to couple to one of primary alignment flanges 128a and 128b. In other embodiments, mating feature 200 may be a single element with alignment flanges 128a and 128b comprising fork elements. In other embodiments, mating feature 200 and alignment flange 128 may implement a ball and socket mating configuration or a hook and latch configuration, for example. In embodiments, needle depth aperture 202 is arranged on bevel cap 120 such that an operator can view the incision depth mark on needle 118.

In embodiments, bevel cap 120 includes one or more needle capture elements 204a-204c. In embodiments and as depicted in FIG. 6c, needle capture elements 204a-204c are configured as a pair of plastic arms to selectively couple to needle 118 via an annular snap fit. While FIG. 6c depicts a cross-section view of needle capture elements 204c, FIG. 6c is representative of other instances of needle capture elements 204. In some embodiments, the needle capture elements 204a-204c are further configured to secure needle 118 via a friction fit sufficient to resist axial movement of needle 118 with respect to carriage 114. In the embodiment depicted in FIGS. 6a-6c, bevel cap 120 includes three needle capture elements 204, although other embodiments may include a different number of needle capture elements 204. In embodiments, bevel cap 120 includes shoulder feature 209 that interfaces with second end 126 of housing 110 to position bevel cap axially relative to an axial orientation of housing 110.

Bevel cap 120 also includes a bevel plug 206 and a needle tip wall 208 arranged at a distal tip of bevel cap 120. Bevel plug 206 is configured to rest within the beveled opening of needle 118. When installed on needle 118 and housing 110, bevel plug 206 is positioned within the beveled opening of needle 118 at a depth such that the bevel plug 206 prevents the RFID tag from exiting needle 118. Needle tip wall 208 is configured to cover the sharp distal tip of needle 118 when bevel cap 120 is installed on needle 118 and primary alignment flanges 128.

Figure 6D:
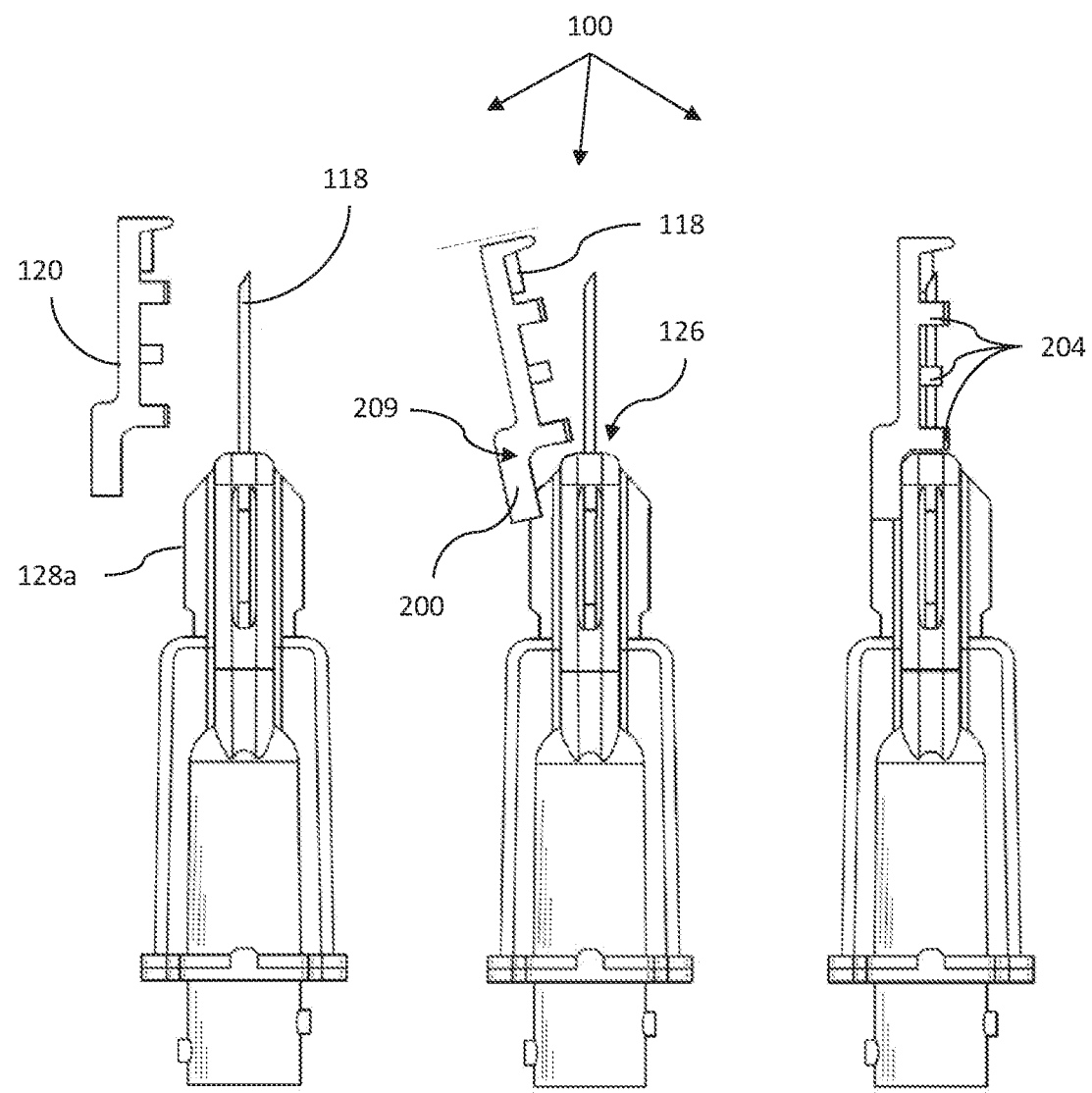
FIG. 6d is a series of side views of a bevel cap being coupled to an RFID tag insertion cartridge, according to embodiments described herein.

In some embodiments, and as depicted in FIG. 6d, housing mating feature 200, needle capture elements 204a-204c, bevel plug 206 and shoulder feature 209 of bevel cap 120 are configured such that bevel cap 120 is installed from an angle orthogonal to the axis of needle 118 as shown in FIG. 6d with the mating feature 200 being engaged first with primary alignment flange 128a or 128b of housing 110 and then the needle capture elements 204a-204c being sequentially engaged with needle 118. Installation of bevel cap 120 from an orthogonal angle ensures that there is little to no axial force placed on needle 118 and carriage 114 during installation of bevel cap 120. In other embodiments, bevel cap 120 is installed in a direction generally transverse to the axis of needle 118 with both the mating feature 200 and needle capture elements being engaged simultaneously with needle 118 and housing 110

Figure 7A:
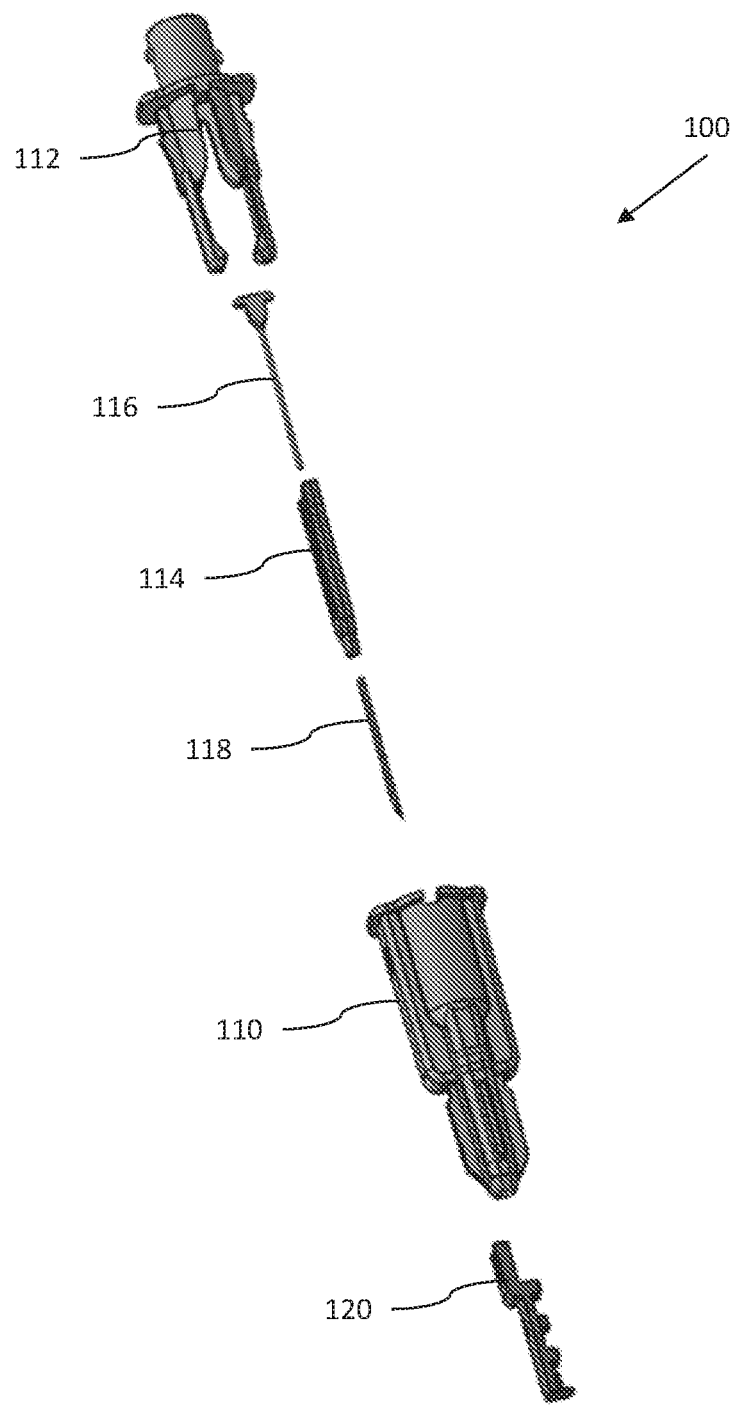
FIG. 7a is an isometric exploded view of an RFID tag insertion cartridge, according to embodiments described herein.
Figure 7B:
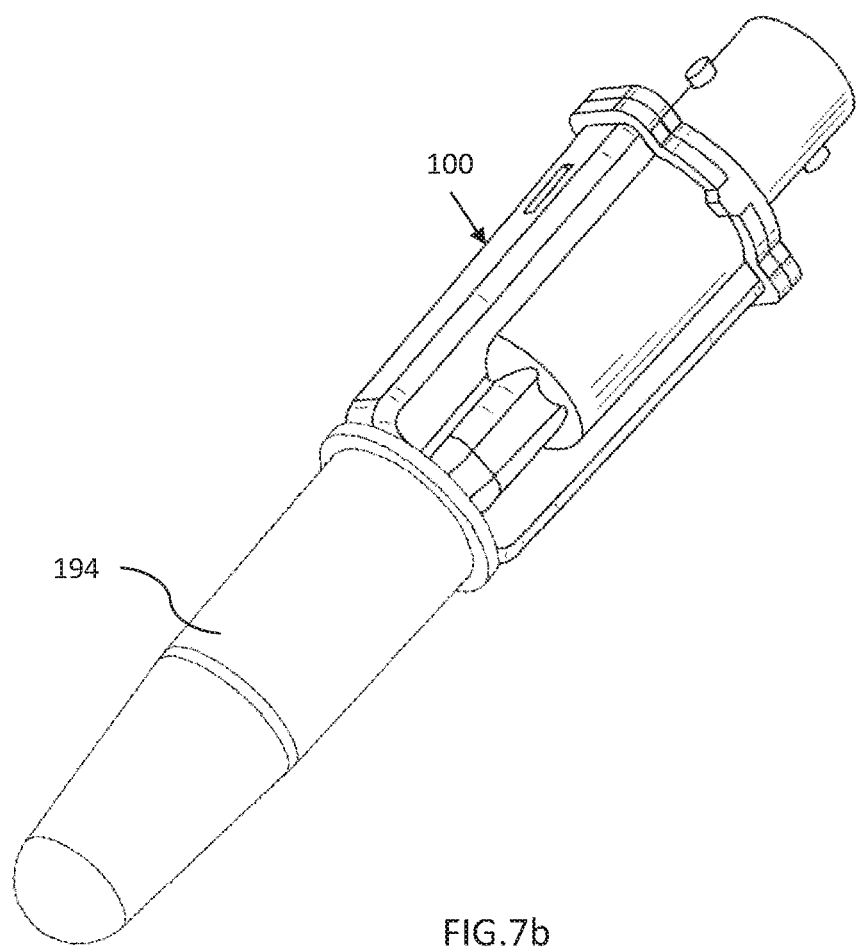
FIG. 7b is an isometric view of an RFID tag insertion cartridge with a safety cap, according to embodiments described herein.

In embodiments and as depicted in FIGS. 7a and 7b, cartridge 100 can be assembled first by coupling needle 118 to carriage 114 at needle mount aperture 138. In embodiments, needle 118 is fixedly coupled to carriage 114 at needle mount aperture 168 such that the beveled opening of needle 118's tip faces towards one of primary alignment flanges 128a and 128b when cartridge 100 is assembled. This orientation of the beveled opening of needle 118 with respect to primary alignment flanges 128a and 128b ensures that bevel plug 206 of bevel cap 120 rest within the beveled opening and therefore securing the RFID tag within needle 118. The carriage 114 and needle 118 sub-assembly can then be placed within housing 110 such that needle 118 is fully extended through needle aperture 138 of housing 110. Then, stop pin 116 can be inserted into housing 110 from first end 124 and guided within stop pin channel 170 of carriage 114. Shaft 182 of stop pin 116 is positioned within needle 118 during insertion. Once stop pin 116 is fully inserted within housing 110, carriage 114 and needle 118, coupling 112 can be aligned and guided into housing 110. Coupling 112 is inserted within housing 110 until coupling alignment tabs 150 and coupling wedges of coupling 112 are positioned within coupling alignment notches 134 and coupling wedge apertures 136, respectively.

Once cartridge 100 is assembled, an RFID tag can be inserted within the distal tip of needle 118 until the RFID tag reaches tag stop surface 184 of stop pin 116. Then, bevel cap 120 and be mounted to needle 118 from an angle orthogonal to the axis of needle 118. Once bevel cap 120 is positioned on needle 118, the RFID tag is secured within needle 118 between tag stop surface 184 and bevel plug 206, and needle 118 is restricted from moving with respect to housing 110. For further security and safety, a safety cap 194 can be placed over needle 118 and bevel cap 120. Safety cap 194 can be secured via press fit at safety cap notch 130 of housing 110.

Figure 8A:
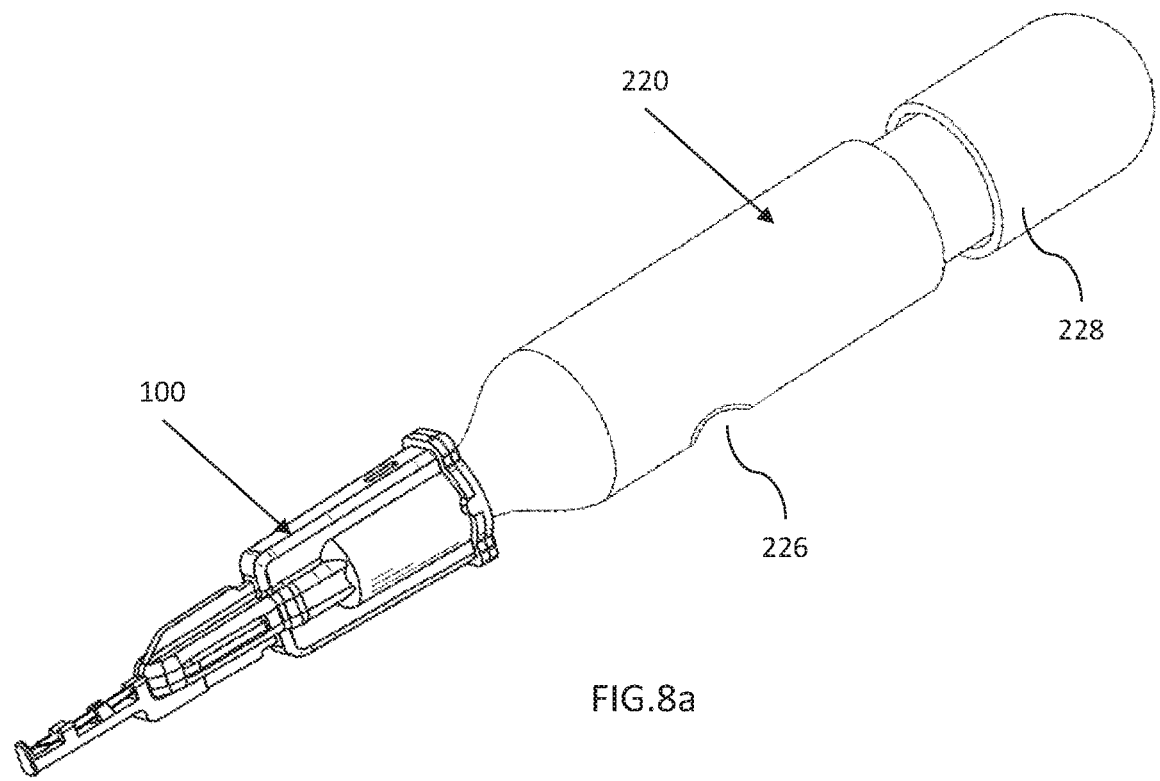
FIG. 8a is an isometric view of an RFID tag insertion cartridge coupled to an RFID tag insertion tool, according to embodiments described herein.
Figure 8B:
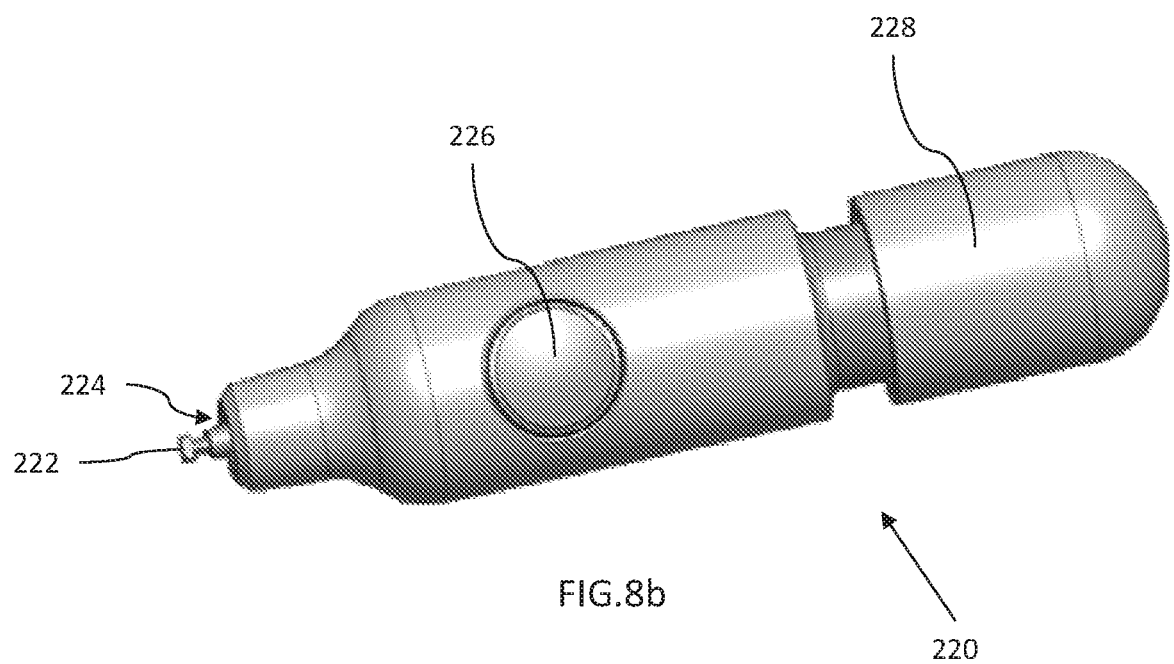
FIG. 8b is an isometric view of an RFID tag insertion tool for use with an RFID tag insertion cartridge, according to embodiments described herein.

As depicted in FIGS. 8a and 8b, cartridge 100 is configured to selectively couple to an RFID tag insertion tool 220 as it is described in WO 2019/071320 A1. In pertinent part, insertion tool 220 includes a carriage coupler 222, a cartridge fitting 224, a button 226 and an actuator 228. For full description of the structure, assembly and functionality of insertion tool 220, refer to WO 2019/071320 A1. In embodiments, carriage coupler 222 is configured to couple to tool coupler notches 176 of carriage 114. Cartridge fitting 224 is configured to selectively receive and couple to tool coupling bosses 148 of coupling 112. In embodiments, cartridge fitting 224 is configured to receive tool coupling bosses 148 in only one orientation by way of the asymmetrical arrangement of tool coupling bosses 148 on coupling 112. For example, if a user attempts to connect cartridge 100 to insertion tool 220 in an incorrect orientation, cartridge 100 will not fully seat and cartridge 100 would be inoperable. If the user connects cartridge 100 to insertion tool 220 in the correct orientation, cartridge 100 will fully seat and cartridge 100 would be operable. Insertion tool 220 is placed in a loaded position by depressing and releasing actuator 228. In the loaded position, carriage coupler 222 is positioned such that the distal tip is located within coupler notches 176 of carriage 114. The user can place insertion tool 220 in an unloaded position by depressing button 226. In the unloaded position, carriage coupler 222 is in an axially receded position.

Embodiments of the improved RFID tag insertion cartridge 100 can be configured for use with improved embodiments of insertion tool 220 than what is disclosed in WO 2019/071320 A1. For example, insertion tool 220 can include varied proportions, such as an elongated cartridge fitting 224 and associated lengthening of insertion tool 220 housing. In use, cartridge 100 is configured to move between a first position and a second position with the aid of the actuation of carriage coupler 222 of insertion tool 220. First position can be defined as a pre-implant position such that needle 118 is fully distally extended. First position also includes the RFID tag being held within needle 118 and between tag stop surface 184 of stop pin 116 and bevel plug 206 of bevel cap 118. Second position can be defined as a disposal position such that needle 118 no longer contains the RFID tag and needle 118 and stop pin 116 are in a receded positioned entirely within housing 110. Thus, cartridge 100 is disposable in the second position as it no longer includes the RFID tag and the needle is no longer exposed.

In the first position, shaft 182 of stop pin 116 is position within needle 118 and positioned towards second end 126 of housing 110 such that stop pin 116 is engaged with housing 110. In the first position also includes the distal surfaces of stop pin tabs 154a and 154b of coupling 112 being engaged with coupling engaging tabs 188a and 188b such that stop pin tabs 154a and 154b prevent stop pin 116 from moving axially. Also in the first position, and when cartridge 100 is coupled to insertion tool 220, carriage coupler 222 is positioned such that the distal tip is located within coupler notches 176 of carriage 114. This is also the loaded position of insertion tool 220.

Prior to insertion of needle 118 within the subject animal, bevel cap 120 is removed. The user can then insert needle 118 within the subject animal until the desired depth is reached in relation to the incision depth mark. The user can then depress button 226 to initiate the transition from the first position to the second position.

Once button 226 is depressed, carriage coupler 222 recedes into insertion tool 220. Because carriage coupler 222 is engaged with carriage 114 at tool coupler notches 176, carriage 114 and needle 118 rapidly recede into housing 110 with the axial movement of carriage coupler 222. During the first portion of axial movement of carriage 114 and needle 118, stop pin 116 remains stationary while stop pin channel 170 of carriage 114 moves around stop pin 116. Stop pin 116 is further held in place via engagement with tab projections 156 of coupling 112. Because stop pin 116 does not move in relation to needle 118 during the first portion of axial movement, the RFID tag remains in position within the flesh of the animal while needle 118 recedes around the RFID tag. The second portion of axial motion begins when stop pin 116 is positioned near second end 166 of carriage 114 such that stop pin engaging surface 172 of carriage 114 engages with coupling engaging surface 186. At this point, stop pin 116 begins to recede with needle 118 and carriage 114. The force of carriage coupler 222 receding into insertion tool 220 forces stop pin 116 to spread stop pin tabs 154 of coupling 112 apart. Stop pin tabs 154 are spread apart enough such that coupling engaging tabs 188 can pass by tab projections 156 of stop pin tabs 154. Second position is reached when both needle 118 and stop pin 116 are positioned entirely within housing 110.

Insertion tool 220 and cartridge 100 are configured such that an operators hand can manipulate insertion tool 220 and cartridge 100 at different angles and orientations while still maintaining intended performance. This is achieved, in part, by the size, shape, and material characteristics of the RFID tag itself. As such, gravity and natural biomechanical forces within the tail of the rodent tend to determine the orientation of the RFID tag. Thus, the orientation of the RFID tag does not need to be precisely controlled during implantation.

Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

The invention claimed is:

1. A radio frequency identification (RFID) tag insertion cartridge configured for use in implanting a flexible RFID tag into a small animal using a needle-retraction implant tool, the cartridge comprising:
   a cartridge housing configured to receive a carriage portion inserted into a first end of the cartridge housing with a retractable needle extended out of a second end of the carriage portion to present the retractable needle in an extended position with the RFID tag carried within the retractable needle; and
   a bevel cap having a proximal portion with a mating feature configured to mate with the cartridge housing and two or more needle capture elements configured to selectively couple to the needle in the extended position in a side-mountable manner without a direct axial force being exerted on the needle, wherein the two or more needle capture elements couple to the needle in a spaced apart configuration along a length of the needle.

2. The RFID tag insertion cartridge of claim 1, wherein the bevel cap is configured to mate with the cartridge housing from an angle orthogonal to an axis of the needle with the mating feature being engaged first with the cartridge housing and then the two or more needle capture elements being engaged with the needle such that there is an effective pivot point at a distal portion of the bevel cap for rotating a proximal portion of the bevel cap onto the needle.

3. The RFID tag cartridge of claim 1, wherein the bevel cap is configured to mate with the cartridge housing from a direction generally transverse to an axis of the needle with the mating feature being engaged with the cartridge housing simultaneous with the two or more needle capture elements being engaged with the needle.

4. The RFID tag cartridge of claim 1, wherein the two or more needle capture elements each comprise a pair of resilient arms that selectively couple to the needle via an annular snap fit.

5. The RFID tag cartridge of claim 1, wherein the two or more needle capture elements each comprise structure that selectively couples to the needle via a friction fit sufficient to resist axial movement of the needle with respect to the carriage housing.

6. The RFID tag cartridge of claims 1, wherein the mating feature comprises a pair of fork elements configured to couple to a single alignment flange on the cartridge housing.

7. The RFID tag cartridge of claims 1, wherein the mating feature comprises a single mating element configured to couple to a pair alignment flanges on the cartridge housing.

8. The RFID tag cartridge of claim 1, wherein the bevel cap includes a shoulder feature that interfaces with the second end of the cartridge housing to position the bevel cap axially relative to an axial orientation of the cartridge housing.

9. The RFID tag cartridge of claim 1, wherein the bevel cap includes:
   a distal tip having a bevel plug configured to rest within a beveled distal opening of the needle to prevent the RFID tag from exiting the beveled distal opening of the needle when the bevel cap is selectively coupled to the needle, and
   a needle tip wall configured to cover a sharp tip of the beveled distal opening of the needle when the bevel cap is selectively coupled to the needle.

10. A radio frequency identification (RFID) tag insertion cartridge configured for use in implanting a flexible RFID tag into a small animal using a needle-retraction implant tool, the cartridge comprising:
   a cartridge housing configured to receive a carriage portion inserted into a first end of the cartridge housing with a retractable needle extended out of a second end of the carriage portion to present the retractable needle in an extended position with the RFID tag carried within the retractable needle; and
   a bevel cap having a proximal portion with a mating feature configured to mate with the cartridge housing and one or more needle capture elements configured to selectively couple to the needle in the extended position in a side-mountable manner without a direct axial force being exerted on the needle,
   wherein the bevel cap is configured to mate with the cartridge housing from an angle orthogonal to an axis of the needle with the mating feature being engaged first with the cartridge housing and then the one or more needle capture elements being engaged with the needle such that there is an effective pivot point at a distal portion of the bevel cap for rotating a proximal portion of the bevel cap onto the needle,
   wherein the one or more needle capture elements each comprise a pair of resilient arms that selectively couple to the needle via an annular snap fit,
   wherein the mating feature comprises a pair of fork elements configured to couple to a single alignment flange on the cartridge housing, and
   wherein the bevel cap includes a shoulder feature that interfaces with the second end of the cartridge housing to position the bevel cap axially relative to an axial orientation of the cartridge housing.

11. A radio frequency identification (RFID) tag insertion cartridge configured for use in implanting a flexible RFID tag into a small animal using a needle-retraction implant tool, the cartridge comprising:
   a cartridge housing configured to receive a carriage portion inserted into a first end of the cartridge housing with a retractable needle extended out of a second end of the carriage portion to present the retractable needle in an extended position with the RFID tag carried within the retractable needle; and
   a bevel cap having a proximal portion with a mating feature configured to mate with the cartridge housing and one or more needle capture elements configured to selectively couple to the needle in the extended position in a side-mountable manner without a direct axial force being exerted on the needle,
   wherein the bevel cap is configured to mate with the cartridge housing from a direction generally transverse to an axis of the needle with the mating feature being engaged with the cartridge housing simultaneous with the one or more needle capture elements being engaged with the needle, wherein the one or more needle capture elements each comprise structure that selectively couples to the needle via a friction fit sufficient to resist axial movement of the needle with respect to the carriage housing, wherein the mating feature comprises a single mating element configured to couple to a pair alignment flanges on the cartridge housing, wherein the bevel cap includes:

a distal tip having a bevel plug configured to rest within a beveled distal opening of the needle to prevent the RFID tag from exiting the beveled distal opening of the needle when the bevel cap is selectively coupled to the needle, and a needle tip wall configured to cover a sharp tip of the beveled distal opening of the needle when the bevel cap is selectively coupled to the needle.

\* \* \* \* \*